United States Patent
Launay et al.

(10) Patent No.: US 6,652,142 B2
(45) Date of Patent: Nov. 25, 2003

(54) METHOD OF CALIBRATION FOR RECONSTRUCTING THREE-DIMENSIONAL MODELS FROM IMAGES OBTAINED BY TOMOGRAPY

(75) Inventors: Laurent Launay, Saint Remy les Chevreuse (FR); Andreas Rick, Schwerte (DE); Serge Muller, Guyancourt (FR); Sophie Seggar, Malakoff (FR)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 76 days.

(21) Appl. No.: 10/091,639

(22) Filed: Mar. 6, 2002

(65) Prior Publication Data

US 2002/0131559 A1 Sep. 19, 2002

(30) Foreign Application Priority Data

Mar. 13, 2001 (FR) .............................. 01 03386

(51) Int. Cl.[7] .......................... H05G 1/60; G01D 18/00
(52) U.S. Cl. ....................... 378/205; 378/21; 378/163; 378/207; 600/426
(58) Field of Search ............................. 378/18, 21, 22, 378/25, 26, 27, 37, 162, 163, 164, 205, 207; 600/426, 429

(56) References Cited

U.S. PATENT DOCUMENTS

| | | | |
|---|---|---|---|
| 4,875,478 A | 10/1989 | Chen | 600/429 |
| 5,359,637 A | 10/1994 | Webber | 378/2 |
| 5,668,844 A | 9/1997 | Webber | 378/2 |
| 5,951,475 A * | 9/1999 | Gueziec et al. | 600/425 |
| 5,964,715 A * | 10/1999 | Thunberg | 600/562 |
| 5,999,840 A * | 12/1999 | Grimson et al. | 600/424 |
| 6,044,132 A * | 3/2000 | Navab | 378/163 |
| 6,049,582 A | 4/2000 | Navah | 378/4 |
| 6,196,715 B1 * | 3/2001 | Nambu et al. | 378/197 |
| 6,289,235 B1 * | 9/2001 | Webber et al. | 600/426 |
| 2003/0043962 A1 * | 3/2003 | Lai | 378/23 |

OTHER PUBLICATIONS

Rizo et al, "Geometric Calibration Method for Multiple Heads Gone–Beam Spect System", Nuclear Science Sympusium and Medical Imaging Conference 1993, 1993 IEEE Conference Record, 310U–Nov. 6, 1993, pp 1764–1768.

* cited by examiner

Primary Examiner—Edward J. Glick
Assistant Examiner—Allen C. Ho
(74) Attorney, Agent, or Firm—Jay L. Chaskin; Cantor Colburn LLP

(57) ABSTRACT

A method of calibration for reconstructing three-dimensional models from images obtained by a tomography apparatus comprising a radiation detector and an X-ray source which can move with respect to the detector. In the method a set of markers are placed in the field of the X-rays and the positions of the projections of the markers onto the images acquired are processed so as to deduce from this the position of the source at the time of acquisitions, the markers being carried by one and the same support. The markers are fixed with respect to the support and the positions of the projections of the markers onto the images acquired are processed so as to deduce from this the position of the markers in space.

8 Claims, 1 Drawing Sheet

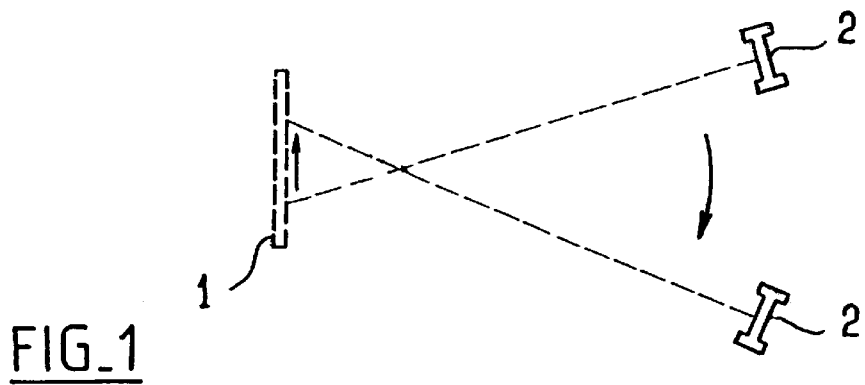
FIG_1
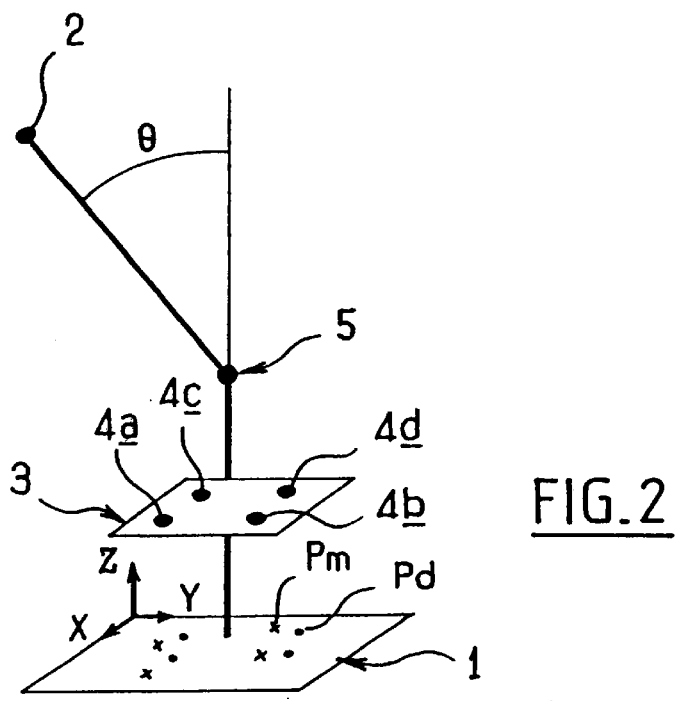
FIG_2
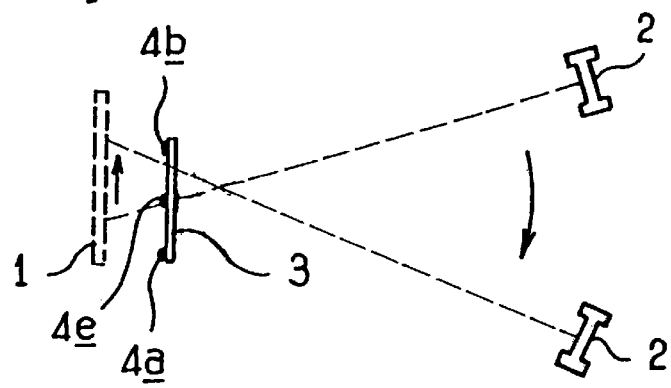
FIG_3
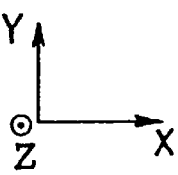

METHOD OF CALIBRATION FOR RECONSTRUCTING THREE-DIMENSIONAL MODELS FROM IMAGES OBTAINED BY TOMOGRAPY

CROSS-REFERENCE TO RELATED APPLICATIONS

This application claims the benefit of a priority under 35 USC 119 to French Patent Application No. 0103386 filed Mar. 13, 2001, the entire contents of which are hereby incorporated by reference.

BACKGROUND OF THE INVENTION

The present invention relates to calibration techniques for image reconstruction of three-dimensional models from images obtained by X-ray tomography.

ConventionaUy, a tomography system comprises, as illustrated in FIG. 1, means for detection 1, (for example, a screen sensitive to X-rays), which may be fixed, and means for providing radiation 2, for example, a source of X-rays which can move and which adopts several positions with respect to the means for detection 1 and to a body or object that is to undergo radiography, the source 2 rotating about a fixed point 5 of the body or of the object.

Numerous techniques for reconstructing three-dimensional models from tomographic two-dimensional images are known. See, for example, a reconstruction algorithm, in "Image reconstruction from projections: the fundamentals of computerized tomography"—T. Herman—Academic Press—New—T. Herman—Academic Press, New York (1980). Such reconstructions generally entail precise "geometric calibration" of the image-acquisition system, this calibration associating the three-dimensional space with the two-dimensional information supplied by the various two-dimensional projections. If this calibration is coarse, the quality of the three-dimensional model reconstructed will exhibit defects; in particular, small structures will appear fuzzy. In certain cases, this calibration is performed directly from information supplied by the image-acquisition system itself, such as the distance between the source and the means for detection, the angular positions of the source, etc. An alternative to this type of calibration comprises carrying out prior calibration of the image-acquisition geometry (without the patient) and in imposing precalibrated successive positions on the source. For mechanical reasons, these types of calibration do not give satisfactory precision or results.

Other calibration techniques use markers which act as references in space and which lie in the field of the X-rays during image acquisitions and therefore appear on the projected images. The positions of these markers in three-dimensional space are supposed to be known and the image acquisition geometry for each projection is deduced by inversion of a system of equations which is derived from the position of the markers on the projected images. In theory, techniques using these markers should give better precision than techniques not using markers. In practice, it is often difficult to determine precisely the position of the markers in space. In particular, during mammography, markers are fixed to a compression plate, whose position with respect to the detector is not known with great precision and which is likely to move slightly as the breast of the patient is compressed.

BRIEF DESCRIPTION OF THE INVENTION

An embodiment of the invention is a method using markers to determine substantially precisely their position in space.

An embodiment of the invention is method of a calibration for reconstructing three-dimensional models from images obtained by a tomography apparatus comprising means for detection and means for providing radiation which can move with respect to the means for detection wherein a set of markers are placed in the field of the radiation and the positions of the projections of the markers onto the images acquired are processed so as to deduce from this the position of the means for providing radiation at the time of the acquisitions, the markers being carried on one and the same support. The markers are fixed with respect to the support and the positions of the projections of the markers onto the images acquired are processed so as to deduce from this the position of the markers in space.

In particular, in an embodiment of the invention, the positions of the projections of the markers onto the images acquired are processed so as to deduce from this conversion parameters which characterize a rigid displacement of the markers between their assumed initial position and a position adopted by the markers following a displacement.

In particular, according to an embodiment, the positions of the radiation source during various image acquisitions and the values of conversion parameters which, for all the markers and acquisitions, minimize an overall error which is a function of the distances between, on the one hand, the theoretical position of the projection of each marker into the image resulting from an acquisition and, on the other hand, its actual position in the image, are determined.

As understood, an embodiment of the method permits obtaining precise calibration substantially without the need initially to know the exact position of the markers in space.

BRIEF DESCRIPTION OF THE DRAWING

Embodiments of the invention will become further apparent from the description which follows, which is purely illustrative and non-limiting and should be read in conjunction with the appended figures, in which:

FIG. 1 illustrates the general principle of a tomography apparatus;

FIGS. 2 and 3 schematically illustrate one possible embodiment of the invention.

DETAILED DESCRIPTION OF THE INVENTION

As illustrated by FIGS. 2 and 3, one possible support for markers 4a to 4d for implementing the invention is a flat plate 3, for example, a compression plate. Markers 4a to 4d are, for example, metal balls, while the plate 3 is made of a material which is transparent to X-rays. During acquisition, an object to be imaged, for example, the breast, is compressed between a screen 1 and the plate 3 bearing the markers 4a to 4d. For each position of the source 2, the radiation emitted by the source projects onto the screen 1 which constitutes the means for detection, an image of the markers 4a to 4d at the same time as an image of the region of the object that undergoes radiography. The exact position of the plate 3 is not known precisely. In particular, the compression achieved when the screen 1 and the plate 3 are placed on the breast leads to a displacement of the plate and this displacement may vary greatly from one patient to another. The only known data are the relative positions of the various markers 4a to 4d with respect to one another. Once the compression plate 3 is in place, it may be considered that it remains fixed throughout the series of image acquisitions performed.

Calibration comprises determining substantially precisely, for each acquisition: the position of the source 2 and the displacement of the plate 3 with respect to its initial position. This corresponds to the determination of 3N+6 acquisition geometry parameters where N is the number of acquisitions, namely: three coordinates of the source 2 for each acquisition, it being possible for these coordinates to be Cartesian coordinates (x, y, z in the figures) or polar coordinates and six parameters describing the rigid conversion that corresponds to the displacement of the plate from its initial position to its actual position (three translational parameters and three rotational parameters). This determination is done using the constraint that the markers are fixed with respect to one another.

For example, the acquisition parameters, for all of the markers and all of the acquisitions, it is possible to minimize the sum of the distances between, the theoretical position Pm of the projection of each marker into the image resulting from an acquisition and its actual position Pd in the image (minimization of the overall error), is determined. The theoretical position Pm is defined as follows:

(1) from the position (x, y, z) assumed to be that of the source, a law of the theoretical projection of the points lying in the field of the source is defined; such a projection law is summarized, for example, as is conventionally the case in viewing software, to a 3×4 projection matrix;

(2) the position of each marker is determined by applying to all of the markers the rigid conversion which is assumed to correspond to the displacement of the plate; and (3) the calculated projection is applied to the calculated position of the markers and from this the theoretical position Pm of the markers on the projected image is deduced. Minimization may be achieved by conventional non-linear minimizing techniques, for example, the Powell method.

Given the large number of unknown parameters, the computation time may be undesirably long. This is why this minimizing is preferably performed by determining the parameters of the rigid conversion on the one hand, and the coordinates corresponding to the various positions (xi, yi, zi) adopted by the source, on the other hand, in two different steps. First, the parameters of the rigid conversion are given initialization values and the source positions for all the acquisitions that minimize the overall error are determined. Secondly, using the source positions thus determined in the first step, six of the rigid conversion parameters which minimize the overall error are determined.

In this iterative process, the step which comprises determining the various positions of the source during the various image acquisitions may be broken down into n independent minimizations. This method of calibration provides the coordinates of the markers in space being determined. When the markers are fixed to a compression plate (in the case of mammography), the method described is fairly insensitive to the movements of the plate during the compression of the breast.

Various modifications in structure and/or steps and/or function may be made by one skilled in the art without departing from the scope and extent of the invention as recited in the claims.

What is claimed is:

1. A method of calibration for constructing three-dimensional models from images acquired by a tomography system comprising means for detection and means for providing a radiation source which can move with respect to the means for detection, comprising:

placing a set of markers in the field of the source;

processing the positions of the projections of the markers onto the images acquired so as to deduce from this the position of the source at the time of the acquisitions, the markers being carried on the same support;

determining the positions of the source during various acquisitions and the values of conversion parameters which, for all the markers and acquisitions, minimize an overall error that is a function of the distances between the theoretical position of the projection of each marker onto the image resulting from an acquisition and its actual position in the image;

fixing the markers with respect to the support; and processing the positions of the projections of the markers onto the images acquired so as to deduce from this the position of the markers in space wherein the positions of the projections of the markers onto the images acquired are processed so as to deduce from this conversion parameters which characterize a rigid displacement of the markers between their assumed initial position and a position adopted by the markers following a displacement.

2. The method of calibration according to claim 1 wherein the minimizing comprises:

allocating given values to the conversion parameters and the positions of the source which, for all the acquisitions and markers and determining for these conversion parameter values the minimization of the global error; and determining the conversion parameter values which, for the source positions thus determined, minimize the overall error.

3. The method of calibration according to claim 2, wherein the determination of the positions of the source, given positions are allocated to all the sources except one, and, for the source, a position which, for all of the markers and for the values allocated to the conversion parameters and for the positions allocated to the other sources, minimizes the global error, is determined, this determination being performed for each of the sources in turn.

4. The method of calibration according to claim 1 wherein the support is a compression plate.

5. A system for reconstruction of acquired images comprising:

means for detection;

means providing a radiation source which can move with respect to the means for detection;

a set of markers placed in the field of the radiation source;

means for carrying the markers on the same support; and means for processing positions of projection of the markers onto the acquired image so as to deduce from this the position of the source at the time of the image acquisition, the means for processing provides the positions of the projections of the marker onto the acquired images are processed so as to deduce from this conversion parameters which characterize a rigid displacement of the markers between their assumed initial position and a position adopted by the markers following a displacement; and the means for processing determines the positions of the source during various image acquisitions and the values of conversion parameters which, for all the markers and image acquisitions, minimize an overall error which is a function of the distances between the theoretical position of the projection of each marker onto the image resulting from an acquisition and its actual position in the image.

6. The apparatus according to claim 5 wherein the means for processing which minimizes the overall error comprises:
   allocating given values to the conversion parameters and the positions of the source which, for all the acquisitions and markers and, determining for these conversion parameters values for the minimization of the global error; and
   determining the conversion parameter values which, for the source positions thus determined, minimize the overall error.

7. The apparatus according to claim 6 wherein the means for processing comprises the determination of the positions of the source, given positions are allocated to all the sources except one, and, for the source, a position which, for all of the markers and for the values allocated to the conversion parameters and for the positions allocated to the other sources, minimizes the global error, is determined, this determination being performed for each of the sources in turn.

8. The apparatus according to claim 5 wherein the means for carrying is a compression plate.

* * * * *